_(12)_ United States Patent
Seiler et al.

(10) Patent No.: US 7,012,085 B2
(45) Date of Patent: Mar. 14, 2006

(54) 1,3 DISUBSTITUTED PYRROLIDINES AS α-2-ADRENOCEPTOR ANTAGONISTS

(75) Inventors: Max Peter Seiler, Riehen (CH); Joachim Nozulak, Heitersheim (DE)

(73) Assignee: Novartis AG, Basel (CH)

( * ) Notice: Subject to any disclaimer, the term of this patent is extended or adjusted under 35 U.S.C. 154(b) by 427 days.

(21) Appl. No.: 10/182,090

(22) PCT Filed: Jan. 26, 2001

(86) PCT No.: PCT/EP01/00861

§ 371 (c)(1),
(2), (4) Date: Jul. 24, 2002

(87) PCT Pub. No.: WO01/55132

PCT Pub. Date: Aug. 2, 2001

(65) Prior Publication Data

US 2003/0008874 A1 Jan. 9, 2003

(30) Foreign Application Priority Data

Jan. 28, 2000 (GB) .............................. 0002100

(51) Int. Cl.
*A61K 31/4439* (2006.01)
*A61K 31/4184* (2006.01)
*C07D 401/06* (2006.01)
*C07D 513/04* (2006.01)
*C07D 498/04* (2006.01)

(52) U.S. Cl. .................. 514/343; 546/208; 546/276.4; 548/125; 548/126; 548/127; 514/361

(58) Field of Classification Search ................ 546/208, 546/276.4; 548/125, 126, 127; 514/343, 361
See application file for complete search history.

(56) References Cited

U.S. PATENT DOCUMENTS 5,185,364 A     2/1993    Debernardis et al. ....... 514/444
5,407,946 A   *   4/1995    Lavielle et al. ............. 514/314

FOREIGN PATENT DOCUMENTS

| EP | 296560 A2 | 12/1988 |
| WO | WO 92 18475 A | 10/1992 |
| WO | WO 92/22527 | 12/1992 |
| WO | WO 95/24391 | 9/1995 |
| WO | WO 00 03714 A | 1/2000 |
| WO | WO 00/27815 | 5/2000 |

OTHER PUBLICATIONS (Chemical Abstracts, Abstract No. 3995b, A.V.El'tsov et al., "N–Aralkyl Derivatives of Phenylpyrrolidines", vol. 34, No. 10, pp. 3344–3351 (1964) (XP 002164442).

Ahn, Kyo Han et al., Bioorg.Med.Chem.Lett., vol. 9, No. 10, pp. 1379–1384 (1999) (XP 004164896).

* cited by examiner

*Primary Examiner*—Kamal A. Saeed
*Assistant Examiner*—Janet L. Coppins
(74) *Attorney, Agent, or Firm*—Joseph J. Borovian; E. Jay Wilusz, Jr.

(57) ABSTRACT

The invention provides compounds of formula (I) wherein $R_0$, $R_1$, $R_2$ and A are as defined in the description, and the preparation thereof. The compounds of formula (I) have high affinity as $\alpha_2$ adrenoceptors and hence are useful as pharmaceuticals.

7 Claims, No Drawings

1,3 DISUBSTITUTED PYRROLIDINES AS α-2-ADRENOCEPTOR ANTAGONISTS

This application is a 371 of International Application PCT/EP 01/00861, filed Jan. 26, 2001.

The present invention relates to novel 1,3-disubstituted pyrrolidines, their preparation, their use as pharmaceuticals and pharmaceutical compositions containing them.

More particularly the invention provides a compound of formula I

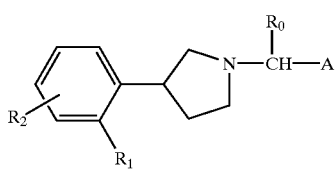

wherein
$R_0$ is hydrogen or $(C_{1-4})$alkyl,
$R_1$ is halogen, hydroxy, $(C_{1-4})$alkyl, $(C_{1-4})$alkoxy, $(C_{2-5})$alkenyloxy, trifluoromethyl or trifluoromethoxy, and can also be hydrogen if A is a group of formula (b), (c), (f) or (g),
$R_2$ is hydrogen or as defined for $R_1$, or, when in ortho position to $R_1$, can also form with $R_1$ a methylenedioxy group, and
A is tetrahydropyran-4-yl or a group of formula

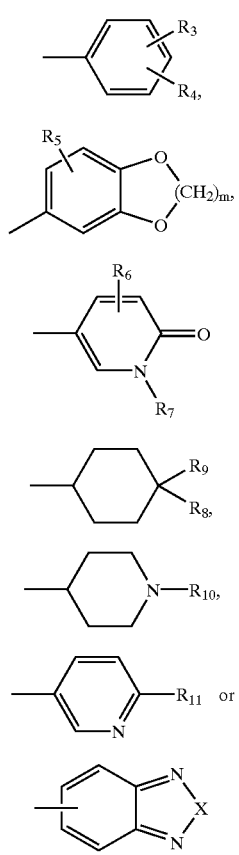

wherein
m is 1 to 3,
X is O, S or CH=CH,
$R_3$ is hydrogen, halogen, hydroxy, $(C_{1-4})$alkyl, hydroxy$(C_{1-4})$alkyl, $(C_{1-4})$alkoxy, trifluoromethyl, $(C_{1-4})$alkylsulfonylamino, benzyloxy, carbamoyl, $(C_{1-4})$alkylcarbamoyl or di$(C_{1-4})$alkylcarbamoyl,
$R_4$ and $R_5$ are hydrogen, halogen, $(C_{1-4})$alkyl or $(C_{1-4})$alkoxy,
$R_6$ is hydrogen, halogen or $(C_{1-4})$alkyl,
$R_7$ is hydrogen, $(C_{1-6})$alkyl or $(C_{3-7})$cycloalkyl$(C_{1-4})$alkyl,
$R_8$ is hydrogen, halogen, hydroxy, $(C_{1-4})$alkyl, $(C_{1-4})$alkoxy, amino, $(C_{2-5})$alkanoylamino, benzoylamino, $(C_{1-4})$alkylsulfonylamino, benzylsulfonylamino, furylcarbonylamino, carbamoyl, $(C_{1-4})$alkylcarbamoyl or di$(C_{1-4})$alkylcarbamoyl, and
$R_9$ is hydrogen, halogen, $(C_{1-4})$alkyl or phenyl, or
$R_8$ and $R_9$ together are —O—$(CH_2)_m$—O— wherein m is as defined above,
$R_{10}$ is hydrogen, $(C_{1-4})$alkyl, $(C_{3-6})$cycloalkyl$(C_{1-4})$alkyl, $(C_{1-4})$alkylcarbonyl, $(C_{3-6})$cycloalkylcarbonyl, $(C_{1-4})$alkoxycarbonyl, benzyl, benzyloxycarbonyl, benzoyl, $(C_{1-4})$alkylsulfonyl, phenylsulfonyl, benzylcarbonyl, benzylsulfonyl, 2-furylcarbonylamino or N—$(C_{1-4})$alkyl-N-(2-furylcarbonyl)amino, and
$R_{11}$ is hydrogen or $(C_{1-4})$alkoxy,
in free base or acid addition salt form.

On account of the asymmetical carbon atom(s) present in the compounds of formula I and their salts, the compounds may exist in optically active form or in form of mixtures of optical isomers, e.g. in form of racemic mixtures. All optical isomers and their mixtures including the racemic mixtures are part of the present invention.

Halogen is fluorine, chlorine, bromine or iodine, preferably fluorine or chlorine.

Any alkyl and alkoxy radicals are branched or straight chain radicals. They are preferably methyl or methoxy groups.

In a further aspect the invention provides a process for the production of the compounds of formula I and their salts, whereby a compound of formula II

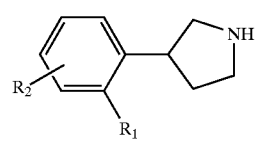

wherein $R_1$ and $R_2$ are as defined above, is alkylated and the resulting compound is recovered in free base form or as an acid addition salt.

The alkylation can be effected in accordance to conventional procedures, for example using an appropriate compound of formula Y—$CHR_O$-A, wherein $R_O$ and A are as defined above and Y is iodine, bromine, chlorine, mesyloxy or tosyloxy, in the presence of a base and in an inert solvent, preferably at elevated temperature, e.g. as described in Example 1. Alternatively a compound $R_o$—CO-A, wherein $R_o$ and A are as defined above, can be used (reductive alkylation), e.g. as described in Example 4. For the preparation of a compound of formula I wherein $R_O$ is hydrogen, the alkylation can also be effected by acylation with an acid A-COOH, wherein A is as defined above, and subsequent reduction, e.g. as described in Example 2.

For the preparation of a compound of formula I wherein A is a group of formula (c) or (e), the substituent $R_7$ or $R_{10}$ may suitably be introduced after the alkylation or acylation/ reduction of the compound of formula II, e.g. as described in Example 3.

Compounds of formula I wherein A is as defined above but free from reduceable functional groups (hereinafter A'), can also be obtained by reduction of a compound of formula III

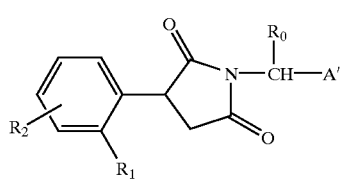

wherein $R_o$, $R_1$, $R_2$ and A' are as defined above, obtained by ring closure of a diacid of formula IV

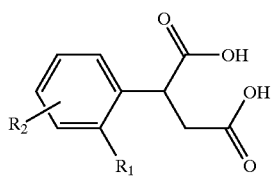

wherein $R_1$ and $R_2$ are as defined above, with an amine $H_2N$—$CHR_0$-A', wherein $R_0$ and A' are as defined above.

Working up of the reaction mixtures obtained according to the above process and purification of the compounds thus obtained may be carried out in accordance to know procedures.

Compounds of formula I in optically pure form can be obtained from the corresponding racemates according to well-known procedures, or using optically pure starting materials, e.g. as described in Examples 2 to 5.

Acid addition salts may be produced in known manner from the free base forms and vice-versa.

The starting compounds of formulae II, IV, Y—$CHR_o$-A and $H_2N$—$CHR_o$-A are known or may be obtained from known compounds, using conventional procedures.

The compounds of formula I and their pharmaceutically acceptable acid addition salts, hereinafter referred to as agents of the invention, exhibit valuable pharmacological properties when tested in vitro and in animals, and are therefore useful as pharmaceuticals.

In binding assays, the agents of the invention display high affinity at $\alpha_2$ adrenoceptor subtypes, with selectivity to $\alpha_{2C}$, as shown in a radioligand binding assay using $^3$H-RX821002 as a ligand and membranes from CHO K1 cells expressing the recombinant human $\alpha_2$ adrenoceptor subtypes. In this assay, agents of the invention exhibit $pK_d$ values of about 6 to about 10.

In in vitro antagonist experiments using cAMP-based luciferase reporter gene assays based on transfected CHO K1 cells stably expressing the recombinant human $\alpha_2$ receptors, in presence of the $\alpha_2$ agonists UK 14,304 or noradrenaline, agents of the invention act as competitive antagonists at the $\alpha_2$ receptors with $pK_B$ values of about 6 to about 9.

In vivo, the agents of the invention inhibit loxapine-induced catalepsy in rats [cf. Kalkman H. O. et al., Br. J. Pharmacol. 124:1550–1556 (1998)] at doses of about 0.3 to about 30 mg/kg s.c.

Furthermore the agents of the invention inhibit amphetamine induced locomotion in rats at doses of about 0.3 to about 30 mg/kg s.c. Locomotion (ambulatory activity) is measured as the number of consecutive infrared interruptions in an appropriate device during a period of 15 min. directly following s.c. injection of amphetamine (1 mg/kg) or solvent (physiological saline) at t=0. The compound or the solvent are administered at t=−30 min.

In view of the above, the agents of the invention are useful as antipsychotics in the treatment of schizophrenia, in the treatment of depression (including bipolar disorders) and more generally in the treatment of any condition associated with a deficiency of noradrenaline in the central or peripheral nervous system which is compensated by α-antagonists via blockade of presynaptic α2 receptors, such as cognition deficits, Parkinson disease, drug abuse, attention deficit hyperactivity disorders, glaucoma, diabetes and erectile dysfunction.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100, preferably from about 0.5 to about 100 mg/kg animal body weight. In larger mammals, for example humans, an indicated daily dosage is in the range from yout 1 to about 500, preferably from about 1 to about 300 mg of an agent of the invention, conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of schizophrenia.

The present invention furthermore provides a pharmaceutical composition comprising an agent of the invention in association with at least one pharmaceutical carrier or diluent. Such compositions may be manufactured in conventional manner. Unit dosage forms contain, for example, from about 0.25 to about 150, preferably from 0.25 to about 25 mg of a compound according to the invention.

For all the above indications, the preferred compounds are (R)-1-isopropyl-5-[3-(2-methoxyphenyl)pyrrolidin-1-ylmethyl]-1H-pyridin-2-one and (R)-1-(2,3,-dihydro-benzo-[1,4]dioxin-6-ylmethyl)-3-(2-methoxyphenyl)pyrrolidine. In the above-mentioned loxapine-induced catalepsy test, both compounds show with 0.3–3 mg/kg s.c. a long lasting, dose-dependent inhibition of catalepsy. An oral dose of 10 mg/kg produces similar inhibition as 3 mg/kg s.c. In the above mentioned amphetamine-induced locomotion test, both compounds dose-dependently reduce locomotion at 0.1, 0.3 and 1 mg/kg s.c. (first mentioned compound) and 1, 3 and 10 mg/kg s.c. (second compound).

The preferred indications are schizophrenia and depression.

Moreover the present invention provides the use of an agent of the invention, for the manufacture of a medicament for the treatment of any condition mentioned above.

In still a further aspect the present invention provides a method for the treatment of any condition mentioned above, in a subject in need of such treatment, which comprises administering to such subject a therapeutically effective amount of an agent of the invention.

The following examples illustrate the invention. The temperatures are given in degrees Celsius and are uncorrected.

EXAMPLE 1

1-(1.4-Dioxaspiro[4.5]dec-8-ylmethyl)-3-(2-methoxyphenyl)pyrrolidine 1 g of 3-(2-Methoxyphenyl)pyrrolidine is dissolved in 60 ml of dioxane and 0.85 g NaI, followed by 1.2 ml of N,N-ethyldiisopropylamine and 1.5 g of 8-bromomethyl-1.4-dioxaspiro[4.5]decane, dissolved in 5 ml of dioxane, are added. The reaction mixture is stirred overnight at 80°, evaporated and the residue extracted with ethylacetate/2N $Na_2CO_3$, followed by aqueous NaCl. The combined, dried and evaporated organic phases yields an oily residue which is purified by flash chromatography on silica gel using t-butylmethylether as a solvent system providing the product as an oil. MS (EI): $M^+$=331; NMR (DMSO): 1.1 (2H, m), 1.45 (3H, m), 1.6–1.8 (5H, m), 2.15 (1H, m), 2.25 (2H, m), 2.4 (1H, t), 2.6 (2H, m), 2.8 (1H, t), 3.6 (1H, t), 3.75 (3H, s), 3.85 (4H, s), 6.9 (2H, dd), 7.15 (1H, t), 7.3 (1H, d).

EXAMPLE 2

(+)-5-[3-(2-methoxyphenyl)pyrrolidin-1-ylmethyl]-1H-pyridin-2-one 10.5 g of (−)-5-[3-(2-methoxyphenyl)pyrrolidin-1-carbonyl]-1H-pyridin-2-one dissolved in 100 ml of THF are added at 0° to a suspension of 6.7 g of $LiAlH_4$ in 200 ml of THF. The temperature of the reaction mixture is allowed to reach room temperature while stirring is continued for 17 hours. Subsequently, the reaction mixture is hydrolysed with $NH_4Cl$ solution and filtered. The filtrate is evaporated and partitioned between $CH_2Cl_2$ and 1N $Na_2CO_3$, followed by aqueous NaCl. The combined organic phases are dried and evaporated and the resulting oil purified by flash chromatography on silica gel using $CH_2Cl_2$/MeOH 9/1 as solvent system providing the product as an oil: $[\alpha_D^{25}]$=+31.4° (c=1.0, EtOH); MS (EI): $M^+$=284; NMR (DMSO): 1.75 (1H, m), 2.15 (1H, m), 2.4 (1H, t), 2.6 (2H, m), 2.8 (1H, t), 3.3–3.4 (2H, m), 3.6 (1H, m), 3.75 (3H, s), 6.3 (1H, d), 6.85–6.95 (2H, m), 7.15 (1H, t), 7.2 (1H, s), 7.25 (1H, d), 7.45 (1H, dd), 11.4 (1H, s).

The starting (−)-5-[3-(2-methoxyphenyl)pyrrolidin-1-carbonyl]-1H-pyridin-2-one is prepared as follows:

6.26 g of 6-hydroxynicotinic acid are suspended in 300 ml of DMF and 9.3 g N,N'-dicyclohexylcarbodiimide, followed by 6.1 g of 1-hydroxybenztriazole are added. After 30 minutes of stirring at room temperature, 8.0 g of (−)-3-(2-methoxyphenyl)pyrrolidine, dissolved in 45 ml of DMF, is added to the resulting solution and stirring continued overnight. Dicyclohexylurea is filtered off, the resulting filtrate evaporated and the residue partitioned between ethylacetate and 2N HCl, followed by aqueous NaCl solution. The combined organic phases are dried and evaporated and the resulting residue purified by flash chromatography on silica gel using $CH_2Cl_2$/MeOH/conc. aqueous $NH_4OH$ 95/4.5/0.5 as solvent system providing the product as a white foam: $[\alpha_D^{25}]$=−34.7° (c=1.0, EtOH); MS (Cl): $MH^+$=299; NMR (DMSO): 2.05 (1H, m), 2.15 (1H, m), 3.45–3.9 (8H, m), 6.35 (1H, d), 6.9–7.05 (2H, m), 7.25 (2H, m), 7.65 (1H, dd), 7.75 (1H, s), 11.9 (1H, s).

EXAMPLE 3

(+)-1-Isopropyl-5-[3-(2-methoxyphenyl)pyrrolidin-1-ylmethyl]-1H-pyridin-2-one and (+)-2-Isopropoxy-5-[3-(2-methoxyphenyl)pyrrolidin-1-ylmethyl]-1H-pyridine 9.75 g of (+)-5-[3-(2-methoxyphenyl)pyrrolidin-1-ylmethyl]-1H-pyridin-2-one (example 2) are dissolved in 170 ml of toluene. 14.2 g of $Na_2CO_3$, followed by 6.9 ml of isopropyl-iodide are added to the solution which is stirred at 100° overnight. Subsequently, another 3.4 g of isopropyliodide are added and stirring continued for additional 17 hours. The reaction solution is extracted with water and the combined organic phases dried and evaporated resulting in an oily residue which is purified by flash chromatography on silica gel using $CH_2Cl_2$/MeOH/conc. aqueous $NH_4OH$ 95/4.5/0.5 as solvent system which provides (+)-1-Isopropyl-5-[3-(2-methoxyphenyl)pyrrolidin-1-ylmethyl]-1H-pyridin-2-one {$[\alpha_D^{25}]$=+19.7° (c=1.0, EtOH); MS (Cl): $MH^+$=327; NMR (DMSO, 120°): 1.3 (6H, d), 1.95 (1H, m), 2.3 (1H, m), 2.7–3.4 (4H, m), 3.6–3.8 (3H, m), 3.8 (3H, s), 5.0 (1H, q), 6.35 (1H, d) 6.9–7.0 (2H, m), 7.2 (1H, t), 7.3 (1H, m), 7.4 (1H, m), 7.6 (1H, m)} and (+)-2-Isopropoxy-5-[3-2-methoxyphenyl)pyrrolidin-1-ylmethyl]-1H-pyridine {$[\alpha_D^{25}]$=+22.8° (c=1.0, EtOH); MS (EI): M+=326; NMR (DMSO): 1.3 (6H, d), 1.75 (1H, m), 2.15 (1H, m), 2.4 (1H, t), 2.65 (2H, m), 2.8 (1H, t), 3.5–3.65 (3H, m), 3.75 (3H, s), 5.2 (1H, m), 6.7 (1H, d), 6.85–6.95 (2H, m), 7.15 (1H, t), 7.3 (1H, d), 7.6 (1H, m), 8.05 (1H, s)}

EXAMPLE 4

(+)-1-(2,3-Dihydrobenz[1.4]dioxin-6-methyl)-3-(2-methoxyphenyl)pyrrolidine 1.77 g of (−)-3-(2-methoxyphenyl)pyrrolidine, followed by 1.8 g of 2,3-dihydrobenz[1.4]-dioxine-6-carbaldehyde are dissolved in 40 ml of MeOH. 1.26 g of $NaCNBH_3$ is added and the reaction mixture stirred during 3 hours at room temperature. The solvent is evaporated and the residue partitioned between ethylacetate and water. The organic phases are combined, dried and evaporated and the resulting oily residue purified by flash chromatography on silica gel using ethylacetate/hexane 1/9 as solvent system. The product is obtained as an oil which is transformed into the hydrochloride salt: mp 201–202°; $[\alpha_D^{20}]$=+9.7° (c=1.0, MeOH); MS (ES): $MH^+$=326; NMR (DMSO/NaOD): 1.7 (1H, m), 2.15 (1H, m), 2.35 (1H, q), 2.6–2.7 (2H, m), 2.8 (1H, t), 3.45 (1H, q), 3.55 (1H, q), 3.75 (3H, s), 4.2 (4H, s), 6.75–6.95 (5H, m), 7.15 (1H, t), 7.25 (1H, d).

EXAMPLE 5

(−)-2-[1-(2,3-Dihydrobenzo[1.4]dioxin-6-ylmethyl)pyrrolidin-3-yl]phenol 450 mg of (−)-2-pyrrolidin-3ylphenol, followed by 520 mg of of 2,3-dihydrobenz[1.4]-dioxine-6-carbaldehyde are dissolved in 10 ml of MeOH. The pH is adjusted to 5.5 by addition of acetic acid and the reaction solution is stirred for 2 hours, before 443 mg of $NaCNBH_3$ is added in portions. Stirring is continued overnight, the solvent subsequently evaporated and the residue purified by flash chromatography on silica gel with $CH_2Cl_2$/EtOH/conc. aqueous $NH_4OH$ 95/4.5/0.5 which provides the product as an oil: $[\alpha_D^{20}]$=−35.6° (c=0.75, EtOH); MS (EI): $M^+$=311; NMR (DMSO): 1.7 (1H, m), 2.2–2.4 (2H, m), 2.6 (1H, t), 2.75 (1H, dd), 2.95 (1H, t), 3.4 (1H, m), 3.6 (2H, q), 4.25 (4H, s), 6.65 (1H, t), 6.7 (1H, d), 6.75–6.85 (3H, m), 6.95–7.05 (2H, m).

The starting (−)-5-[3-(2-methoxyphenyl)pyrrolidin-1-carbonyl]-1H-pyridin-2-one is prepared as follows:

500 mg of (−)-3-(2-methoxyphenyl)pyrrolidine are dissolved in 12 ml of $CH_2Cl_2$, 8.5 ml of a 1 M $BBr_3$ solution in $CH_2Cl_2$ is addded dropwise at 0° and stirring continued overnight. The reaction mixture is poured on 1N $Na_2CO_3$ solution, extracted with $CH_2Cl_2$ and the organic phases washed with brine, dried, evaporated and purified by flash chromatography on silica gel with $CH_2Cl_2$/EtOH/conc. aqueous $NH_4OH$ 88/10.8/1.2 providing the product as an oil: MS (EI): $M^+$=163; NMR (DMSO, 120°): 1.85 (1H, m), 2.2 (1H, m), 2.8 (2H, broad), 2.95–3.05 (2H, m), 2.2–2.4 (2H, m), 3.5 (1H, m), 6.7 (1H, t), 6.8 (1H, d), 7.05 (1H, m), 7.1 (1H, dd).

EXAMPLE 6

1-Benzyl-3-(5-chloro-2-methoxyphenyl)pyrrolidine 730 mg of 1-benzyl-3-(5-chloro-2-methoxyphenyl) pyrroline-2,5-dione are dissolved in 2 ml of acetylchloride and stirred at room temperature for 24 hours. The acetylchloride is evaporated, the residue dried and added to a suspension of 295 mg of $LiAlH_4$ in 15 ml of ether. The reaction mixture is stirred during 30 minutes, hydrolyzed, filtered and partitioned between $CH_2Cl_2$ and 2N $Na_2CO_3$, followed by aqueous NaCl. The combined, dried and evaporated organic phases yield an oil which is purified by flash chromatography using ethylacetate/hexane 1/1 providing the product as a colorless oil: MS (Cl): $MH^+$=302; NMR (DMSO): 1.7 (1H, m), 2.2 (1H, m), 2.4–2.8 (5H, m), 3.6 (2H, q), 3.75 (3H, s), 6.95 (1H, d), 7.15–7.35 (7H, m).

The starting 1-Benzyl-3-(5-chloro-2-methoxyphenyl) pyrroline-2,5-dione is prepared as follows:

1.0 g of 2-(5-chloro-2-methoxyphenyl)succinic acid is suspended in 50 ml of xylene, 0.47 ml of benzylamine is added and the mixture refluxed for 8 hours with separation of water. The solvent is evaporated and the residue taken up in ethylacetate and extracted with 2N HCl, followed by 2N NaOH and aqueous NaCl. The organic layer is dried, filtered and the solvent evaporated. The dried residue is purified by flash chromatography using t-butylmethylether/hexane 1/1 providing the amorphous product: MS (EI): $M^+$=329; NMR (DMSO): 2.65 (1H, dd), 3.1 (1H, dd), 3.45 (3H, s), 4.2 (1H, dd), 4.6 (2H, s), 7.0 (1H, d), 7.25–7.4 (7H, m).

The following compounds of formula I wherein $R_0$, $R_1$, $R_2$ and A have the significancies indicated in the table are produced analogously to Example 1. The compounds marked "A" under "Remarks" are preferably produced analogously to Example 2, the compounds marked "B" preferably analogously to Example 4 or 5, and the compounds marked "C" preferably analogously to Example 3.

| Ex. | $R_0$ | $R_1$ | $R_2$ | A | $[\alpha_D]$ | MS | Remarks |
|---|---|---|---|---|---|---|---|
| 7 | H | OMe | H | a; $R_3$=p-OH, $R_4$=H | +/− | 284 ($MH^+$/FAB) | |
| 8 | " | " | " | a; $R_3$=$R_4$=H | +/− | 268 ($MH^+$/FAB) | 1 |
| 9 | " | " | " | a; $R_3$=o-Cl, $R_4$=H | +/− | 301 ($M^+$/EI) | |
| 10 | " | O-CH-$(CH_3)_2$ | " | a; $R_3$=$R_4$=H | +/− | 295 ($M^+$/EI) | |
| 11 | " | O-$CH_2$-CH=$CH_2$ | " | " | +/− | 293 ($M^+$/EI) | |
| 12 | " | OMe | " | a; $R_3$=m-OMe, $R_4$=H | +/− | 298 ($MH^+$/FAB) | |
| 13 | " | " | " | a; $R_3$=p-$C(CH_3)_3$; $R_4$=H | +/− | 323 ($M^+$/EI) | |
| 14 | " | " | " | d; $R_8$=$R_9$=H | +/− | 273 ($M^+$/EI) | |
| 15 | " | " | " | b; m=1, $R_5$=H | +/− | 311 ($M^+$/EI) | |
| 16 | Me | " | " | a; $R_3$=$R_4$=H | +/− | 281 ($M^+$/EI) | |
| 17 | H | " | " | a; $R_3$=3-OMe, $R_4$=5-OMe | +/− | 327 ($M^+$/EI) | A |
| 18 | " | " | " | d; $R_8$=benzyl-sulfonylamino, $R_9$=H | +/− | 456 ($M^+$/EI) | |
| 19 | " | " | " | d; $R_8$=OMe, $R_9$=H | +/− | 303 ($M^+$/EI) | |
| 20 | " | " | " | e; $R_{10}$=-COOC$(CH_3)_3$ | +/− | 375 ($MH^+$/ES) | |
| 21 | " | " | " | e; $R_{10}$=benzoyl | +/− | 379 ($MH^+$/ES) | |
| 22 | " | " | " | d; $R_8$=OH, $R_9$=Me | +/− | 303 ($M^+$/EI) | |
| 23 | " | " | " | d; $R_8$=OH, $R_9$=phenyl | +/− | 366 ($MH^+$/ES) | |
| 24 | " | " | " | d; $R_8$=benzoyl-amino, $R_9$=H | +/− | 393 ($MH^+$/ES) | |
| 25 | " | " | " | d; $R_8$=-NHCOMe, $R_9$=H | +/− | 331 ($MH^+$/ES) | |
| 26 | " | " | " | a; $R_3$=p-$CH_2OH$, $R_4$=H | +/− | 298 ($MH^+$/ES) | A |
| 27 | " | " | " | a; $R_3$=p-F, $R_4$=H | +/− | 285 ($M^+$/EI) | |
| 28 | " | " | " | a; $R_3$=m-$NHSO_2$-Me, $R_4$=H | +/− | 361 ($MH^+$/ES) | |
| 29 | " | " | " | a; $R_3$=p-$CON(CH_3)_2$, $R_4$=H | +/− | 338 ($M^+$/EI) | |
| 30 | " | " | 5-F | a; $R_3$=$R_4$=H | +/− | 285 ($M^+$/EI) | 2 |

-continued

| Ex. | R₀ | R₁ | R₂ | A | [α_D] | MS | Remarks |
|---|---|---|---|---|---|---|---|
| 31 | " | " | 5-Me | " | +/− | 281 (M⁺/EI) | 3 |
| 32 | " | " | 5-OMe | " | +/− | 297 (M⁺/EI) | |
| 33 | " | " | 4-OMe | " | +/− | 297 (M⁺/EI) | |
| 34 | " | " | 3-OMe | " | +/− | 297 (M⁺/EI) | |
| 35 | " | " | H | d; R₈=-NHCO-2-furyl, R₉=H | +/− | 382 (M⁺/EI) | |
| 36 | " | " | " | f; R₁₁=H | +/− | 268 (M⁺/EI) | A |
| 37 | " | " | " | c; R₆=H, R₇=Me | +/− | 298 (M⁺/EI) | A |
| 38 | " | " | " | d; R₈=R₉=F | +10.3° (c=1/EtOH) | 309 (M⁺/EI) | |
| 39 | " | " | 6-OMe | a; R₃=R₄=H | +/− | 297 (M⁺/EI) | |
| 40 | " | " | H | c; R₆=H, R₇=cyclo-propylmethyl | +19.3° (c=1/EtOH) | 339 (MH⁺/ES) | A |
| 41 | " | " | 3-Me | a; R₃=R₄=H | +/− | 282 (MH⁺/ES) | |
| 42 | " | " | H | a; R₃=3-OMe, R₄=4-OMe | +25.0° (c=0.5/EtOH) | 328 (MH⁺/CI) | |
| 43 | " | " | " | c; R₆=H, R₇=propyl | −18.4° (c=0.9/EtOH) | 327 (MH⁺/ES) | A |
| 44 | " | " | " | a; R₃=m-CON(CH₃)₂; R₄=H | +19.3° (c=1/EtOH) | 338 (M⁺/EI) | |
| 45 | " | -O-CH₂-O- | | a; R₃=R₄=H | +/− | 281 (M⁺/EI) | |
| 46 | " | OMe | H | tetrahydropyran-4-yl | +11.4° (c=1/EtOH) | 275 (M⁺/EI) | A |
| 47 | " | " | " | g; X=O, X-containing ring in 2, 3 | +/− | 309 (M⁺/EI) | B |
| 48 | " | " | " | g; X=O, X-containing ring in 3, 4 | +20.2° (c=0.4/EtOH) | 326 (MH⁺/CI) | |
| 49 | " | " | " | b; m=3, R₅=H | +24.5° (c=1/EtOH) | 340 ° | |
| 50 | " | " | " | g; X=CH=CH, X-containing ring in 3, 4 | +11.7° (c=0.5/EtOH) | 320 (MH⁺/ES) | |
| 51 | " | H | " | b; m=2, R₅=H | +/− | 296 (MH⁺/ES) | B |
| 52 | " | Me | " | " | +/− | 309 (M⁺/EI) | B |
| 53 | " | H | 4-OMe | c; R₆=H, R₇=isopropyl | +/− | 326 (M⁺/EI) | C |
| 54 | " | " | 4-Cl | " | +/− | 331 (MH⁺/ES) | C |
| 55 | " | OMe | 5-F | " | +14.5° (c=1/EtOH) | 345 (MH⁺/ES) | C |
| 56 | " | " | 6-OMe | b; m=2, R₅=H | +/− | 356 (MH⁺/ES) | B |
| 57 | " | OCF₃ | H | " | +/− | 380 (MH⁺/ES) | B |
| 58 | " | CF₃ | H | " | +/− | 364 (MH⁺/ES) | B |
| 59 | " | H | 4-CF₃ | " | +/− | 363 (M⁺/EI) | B |
| 60 | " | OMe | 3-Me | c; R₆=H, R₇=isopropyl | +/− | 341 (MH⁺/ES) | C |
| 61 | " | " | 5-Me | b; m=2, R₅=H | +/− | 340 (MH⁺/ES) | 4, B |
| 62 | " | H | 4-F | c; R₆=H, R₇=isopropyl | +32.0° (c=1/EtOH) | 315 (MH⁺/ES) | C |
| 63 | " | F | H | " | +/− | 315 (MH⁺/EI) | C |

Mp = methyl
1: Mp = 138° (hydrogenfumarate)
2: Mp = 142–440° (hydrogenfumarate)
3: Mp = 146–149° (hydrogenfumarate)
4: Mp = 164–149° (hydrochloride)

What is claimed is:

1. A compound of formula I

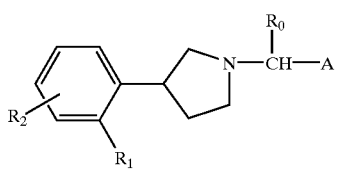

wherein

R$_0$ is hydrogen or (C$_{1-4}$)alkyl;

R$_1$ is halogen, hydroxy, (C$_{1-4}$)alkyl, (C$_{1-4}$)alkoxy, (C$_{2-5}$)alkenyloxy, trifluoromethyl or trifluoromethoxy, and can also be hydrogen if A is a group of formula (c), (f) or (g);

R$_2$ is hydrogen or as defined for R$_1$ or, when in ortho position to R$_1$, can also form with R$_1$ a methylenedioxy group; and A is a group of formula

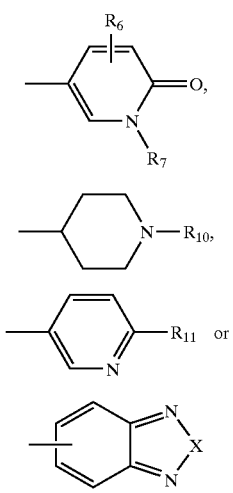

wherein

X is O, S or CH=CH;

R$_6$ is hydrogen, halogen or (C$_{1-4}$)alkyl;

R$_7$ is hydrogen, (C$_{1-4}$)alkyl or (C$_{3-7}$)cycloalkyl(C$_{1-4}$)alkyl;

R$_{10}$ is hydrogen, (C$_{1-4}$)alkyl, (C$_{3-6}$)cycloalkyl(C$_{1-4}$)alkyl, (C$_{1-4}$)alkylcarbonyl, (C$_{3-6}$)cycloalkylcarbonyl, (C$_{1-4}$)alkoxycarbonyl, benzyl, benzyloxycarbonyl, benzoyl, (C$_{1-4}$)alkylsulfonyl, phenylsulfonyl, benzylcarbonyl, benzylsulfonyl, 2-furylcarbonylamino or N—(C$_{1-4}$)alkyl-N-(2-furylcarbonyl)amino; and R$_{11}$ is hydrogen or (C$_{1-4}$)alkoxy, in free base or acid addition salt form.

2. A process for the production of a compound of formula I as defined in claim 1, which comprises alkylating a compound of formula II

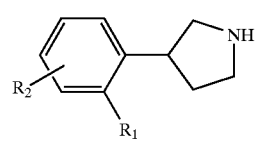

wherein R$_1$ and R$_2$ are as defined in claim 1, and recovering the resulting compound in free base form or as an acid addition salt.

3. A compound of formula I as defined in claim 1, wherein A is a group of formula (c), in free base or acid additional salt form.

4. (S)-1-isopropyl-5-[3-(2-methoxyphenyl)pyrrolidin-1-ylmethyl]-1H-pyridin-2-one in free base or acid addition salt form.

5. A pharmaceutical composition comprising a pharmaceutically acceptable carrier or diluent and a therapeutically effective amount of a compound according to claim 1, in free base or pharmaceutically acceptable salt form.

6. A method of treating a disease or condition which is responsive to an α2 adrenoceptor antagonist in a subject in need of such treatment, selected from the group consisting of schizophrenia, depression, Parkinson's disease, cognition deficits, drug abuse, attention deficit hyperactivity disorders, glaucoma, diabetes, and erectile dysfunction, which comprises administering to such subject a therapeutically effective amount of a compound of claim 1, in free base or pharmaceutically acceptable acid addition salt form.

7. 5-[(R)-3-(4-Fluorophenyl)pyrrolidin-1-ylmethyl]-1-isopropyl-1H-pyridin-2-one, in free base or acid addition salt form.

* * * * *